United States Patent
Mintz et al.

(10) Patent No.: US 10,946,167 B2
(45) Date of Patent: Mar. 16, 2021

(54) CATHETER HUB AND STRAIN RELIEF

(71) Applicant: Covidien LP, Mansfield, MA (US)

(72) Inventors: Eric Mintz, Costa Mesa, CA (US);
David P. Marchesiello, Laguna Niguel, CA (US)

(73) Assignee: Covidien LP, Mansfield, MA (US)

( * ) Notice: Subject to any disclaimer, the term of this patent is extended or adjusted under 35 U.S.C. 154(b) by 190 days.

(21) Appl. No.: 16/008,522

(22) Filed: Jun. 14, 2018

(65) Prior Publication Data

US 2019/0381275 A1 Dec. 19, 2019

(51) Int. Cl.
| | |
|---|---|
| *A61M 25/16* | (2006.01) |
| *A61M 25/18* | (2006.01) |
| *A61M 39/00* | (2006.01) |
| *A61M 39/10* | (2006.01) |
| *A61M 25/00* | (2006.01) |

(52) U.S. Cl.
CPC .... *A61M 25/0014* (2013.01); *A61M 25/0097* (2013.01); *A61M 2025/0098* (2013.01)

(58) Field of Classification Search
CPC ...... A61M 25/0097; A61M 2025/0098; A61M 25/0014; A61M 25/0009
See application file for complete search history.

(56) References Cited

U.S. PATENT DOCUMENTS

| | | |
|---|---|---|
| 5,830,401 A | 11/1998 | Prichard et al. |
| 5,833,275 A | 11/1998 | Andersen |
| 6,273,404 B1 * | 8/2001 | Holman ............ A61M 25/0009 264/259 |
| 7,217,256 B2 | 5/2007 | Di Palma |
| 7,387,624 B2 | 6/2008 | Nelson |

(Continued)

FOREIGN PATENT DOCUMENTS

| | | |
|---|---|---|
| DE | 202004015957 U1 | 2/2005 |
| GB | 2538124 A | 11/2016 |
| JP | 2017-51211 | 3/2017 |

OTHER PUBLICATIONS

Medtronic Inc., "Intracranial Support Catheters," ARC Product, 2017, 2 pp. (Applicant points out, in accordance with MPEP 609.04(a), that the year of publication, 2017, is sufficiently earlier than the effective U.S. filing date, so that the particular month of publication is not in issue.).

(Continued)

*Primary Examiner* — Rebecca E Eisenberg
(74) *Attorney, Agent, or Firm* — Shumaker & Sieffert, P.A.

(57) ABSTRACT

A hub defines a lumen with a longitudinal axis along the length of the hub. An outer surface of a distal portion of the hub tapers inwardly toward the longitudinal axis as the distal portion extends distally. A strain relief includes a proximal portion configured to receive the distal portion of the hub. The strain relief defines a lumen that substantially aligns with the hub lumen when the proximal portion receives the hub. The hub and/or strain relief are configured to be fixedly attached to a catheter body such that a catheter body lumen substantially aligns with the hub lumen and the strain relief lumen when the strain relief receives the distal portion of the hub. Outer surfaces of the strain relief and hub define substantially similar distances to the longitudinal axis along an interface between the two outer surfaces when the strain relief receives the hub.

9 Claims, 10 Drawing Sheets

(56) References Cited

U.S. PATENT DOCUMENTS

| | | | |
|---|---|---|---|
| 7,678,101 B2 | 3/2010 | Sage | |
| 8,152,791 B2 | 4/2012 | Goode et al. | |
| 8,177,772 B2 * | 5/2012 | Christensen | A61M 25/0075 |
| | | | 604/246 |
| 8,409,164 B2 | 4/2013 | Fangrow | |
| 9,017,308 B2 | 4/2015 | Klisch et al. | |
| 2003/0125713 A1 | 7/2003 | McGlinch et al. | |
| 2007/0197956 A1 | 8/2007 | Le et al. | |
| 2008/0125756 A1 | 5/2008 | Dicarlo et al. | |
| 2014/0025044 A1 * | 1/2014 | Zamarripa | A61M 25/0097 |
| | | | 604/533 |
| 2016/0346503 A1 | 12/2016 | Jackson et al. | |
| 2016/0375222 A1 * | 12/2016 | Wada | A61M 25/0097 |
| | | | 604/524 |
| 2017/0014618 A1 | 1/2017 | Ueda | |

OTHER PUBLICATIONS

Medtronic Inc., "Arc Support Catheter Series Ordering Information," 2017, 1 pp. (Applicant points out, in accordance with MPEP 609.04(a), that the year of publication, 2017, is sufficiently earlier than the effective U.S. filing date, so that the particular month of publication is not in issue.).

Extended Search Report from counterpart European Application No. 19175707.9 dated Nov. 15, 2019, 8 pp.

Response to Rules 70(2) and 70a(2) dated Jan. 2, 2020, from counterpart European Application No. 19175707.9, filed Jun. 11, 2020, 50 pp.

* cited by examiner

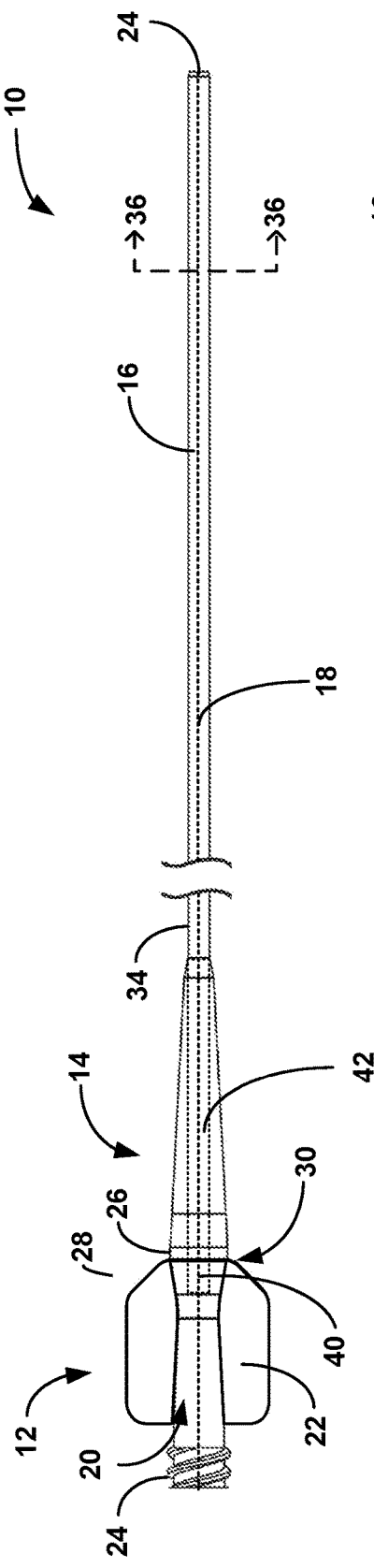
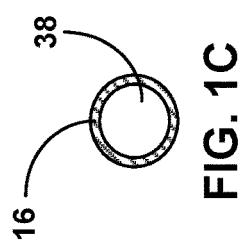
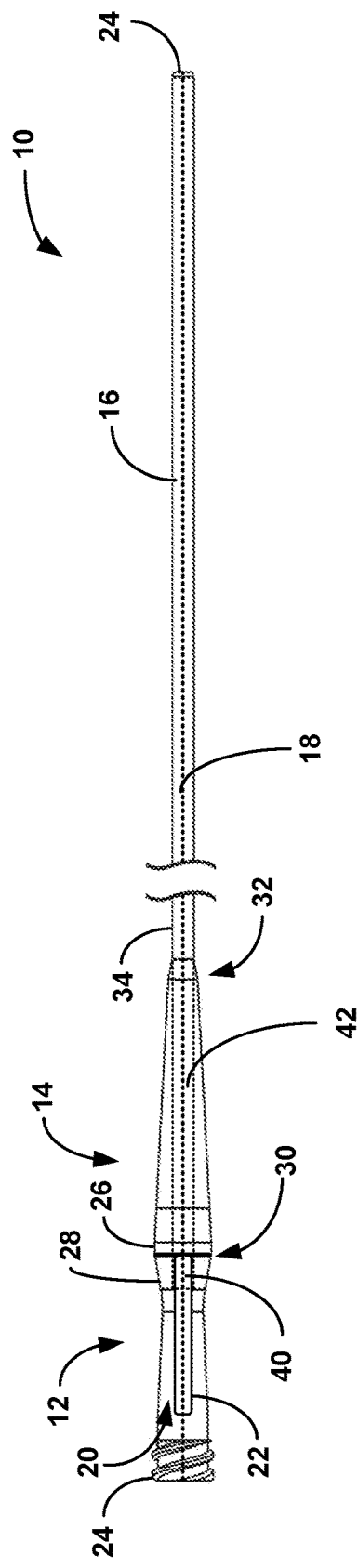

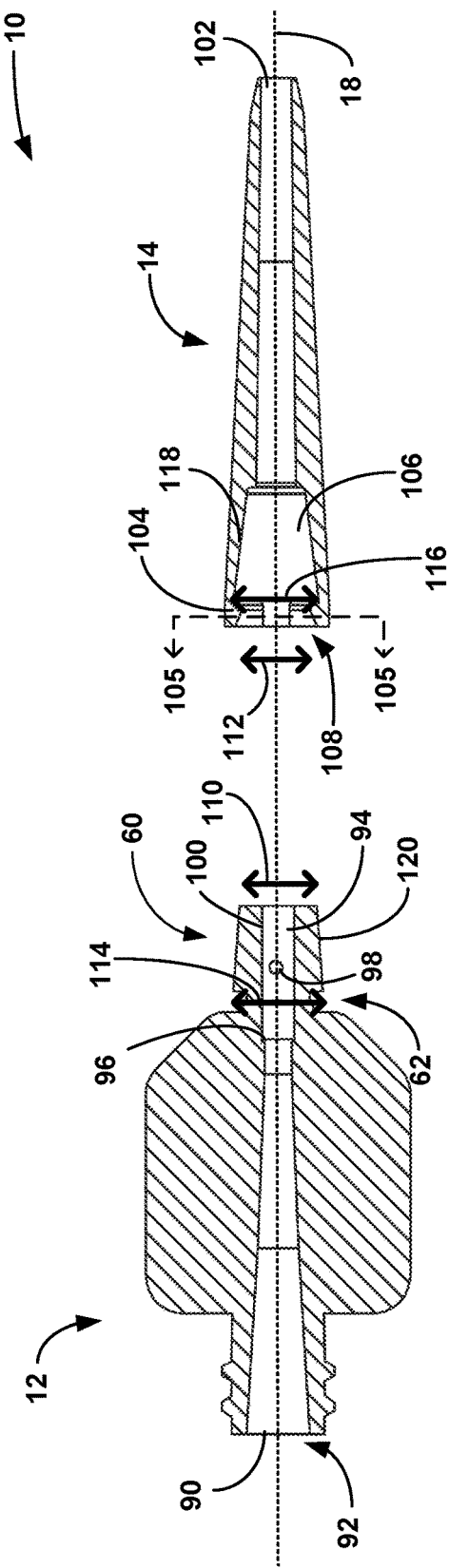

CATHETER HUB AND STRAIN RELIEF

TECHNICAL FIELD

This disclosure relates to a hub and a strain relief for a medical catheter.

BACKGROUND

Medical catheters that define at least one lumen find use in many medical procedures. For example, a medical catheter may be used to transport a fluid such as a drug or a medical agent (e.g., such as a contrast agent) to a target site within a patient. Alternatively, or additionally, a medical catheter may be used to transport an insertable or implantable medical device, a guidewire, or the like to a target site within a patient.

SUMMARY

In some aspects, this disclosure describes medical devices that include a hub and a strain relief. The hub may define a hub lumen that extends from a proximal portion of the hub to a distal portion of the hub. The hub may include a longitudinal axis extending from a proximal end of the hub to a distal end of the hub at a centerline of the hub lumen. An outer surface of the distal portion of the hub tapers inwardly toward the longitudinal axis as the distal portion extends distally. The strain relief may include a proximal portion configured to receive the distal portion of the hub within the strain relief. The strain relief defines a strain relief lumen that substantially aligns with the hub lumen when the proximal portion of the strain relief receives the distal portion of the hub. The strain relief lumen shares the longitudinal axis of the hub when the proximal portion of the strain relief receives the distal portion of the hub. At least one of the hub and strain relief are configured to securely receive a proximal end of a catheter such that a catheter lumen of the catheter substantially aligns with the hub lumen when the strain relief receives the distal portion of the hub. Both an outer surface of the strain relief and an outer surface of a medial portion of the hub define a substantially similar distance to the longitudinal axis along an interface between the outer surface of the strain relief and the outer surface of the hub. In this way, a hub and strain relief may minimize the definition of outward-extending ridges as the hub and strain relief are secured to the catheter, therein reducing a chance that the hub and/or strain relief may "catch" or "snag" on an outside object during an operational procedure that includes the catheter to potentially disrupt this procedure.

Clause 1: In one example, a medical device includes a hub that defines a hub lumen that extends from a proximal portion of the hub to a distal portion of the hub and a longitudinal axis extending from a proximal end of the hub to a distal end of the hub at a centerline of the hub lumen, wherein an outer surface of the distal portion of the hub tapers inwardly toward the longitudinal axis as the distal portion extends distally; and a strain relief, wherein the strain relief comprises a proximal portion configured to receive the distal portion of the hub within the strain relief, wherein the strain relief defines a strain relief lumen that substantially aligns with the hub lumen when the proximal portion of the strain relief receives the distal portion of the hub, wherein at least one of the hub and strain relief are configured to securely receive a proximal end of a catheter body such that a catheter body lumen of the catheter body substantially aligns with the hub lumen when the strain relief receives the distal portion of the hub, and wherein the strain relief lumen shares the longitudinal axis of the hub when the proximal portion of the strain relief receives the distal portion of the hub, and wherein both an outer surface of the strain relief and an outer surface of a medial portion of the hub define a substantially similar distance to the longitudinal axis along an interface between the outer surface of the strain relief and the outer surface of the hub.

Clause 2: In some examples of the medical device of clause 1, the hub comprises a recess comprising a recess surface that is a smaller distance from the longitudinal axis immediately proximal to the distal portion of the hub, wherein an inner surface of the strain relief comprises one or more flanges sized and shaped to extend into the recess to removably secure the strain relief to the hub when the proximal portion of the strain relief receives the distal portion of the hub.

Clause 3: In some examples of the medical device of clause 2, the one or more flanges comprises a plurality of flanges that are arranged around an inner perimeter of the strain relief.

Clause 4: In some examples of the medical device of any of clauses 1-3, the outer surface of the strain relief inwardly tapers to a radius that is substantially similar to an outer radius of the catheter body as the strain relief extends distally.

Clause 5: In some examples of the medical device of any of clauses 1-4, the proximal portion of the strain relief receives the distal portion of the hub with an interference fit between the outer surface of the distal portion of the hub and an inner surface of the proximal portion of the strain relief.

Clause 6: In some examples of the medical device of any of clauses 1-5, the inner surface of the proximal portion of the strain relief defines a cavity configured to receive the distal portion of the hub, wherein the inner surface of the proximal portion of the strain relief tapers inward toward the longitudinal axis as the cavity extends distally, wherein the inner surface of the proximal portion of the strain relief tapers inwardly with a relatively greater slope than the distal portion of the hub as the distal portion tapers inwardly to define the interference fit.

Clause 7: In some examples of the medical device of clause 6, a radius of a proximal edge of the distal portion of the hub is substantially equal to a radius of a proximal edge of the cavity of the strain relief.

Clause 8: In some examples of the medical device of clause 7, the hub comprises a recess comprising a recess surface that is a smaller distance from the longitudinal axis immediately proximal to the distal portion of the hub than the radius of a proximal edge of the distal portion of the hub, wherein an inner surface of the strain relief comprises one or more flanges sized and shaped to extend into the recess to removably secure the strain relief to the hub when the proximal portion of the strain relief receives the distal portion of the hub, wherein the one or more flanges extend radially into the recess a radius that is smaller than the radius of a proximal edge of the distal portion of the hub such that the one or more flanges are configured to engage the proximal edge.

Clause 9: In some examples of the medical device of any of clauses 1-8, the hub defines two wings that extend outward from an outer surface of the hub.

Clause 10: In some examples of the medical device of any of clauses 1-9, a proximal end of the hub includes a Luer lock.

Clause 11: In some examples of the medical device of any of clauses 1-10, a force that is required to proximally move the strain relief over the distal portion of the hub to receive the distal portion of the hub increases as the strain relief moves proximally over the distal portion due to the taper of the outer surface of the distal portion of the hub.

Clause 12: In some examples of the medical device of any of clauses 1-11, an outer surface of the medial portion of the hub tapers radially inwardly as the medial portion extends proximally from the distal portion to the proximal portion.

Clause 13: In some examples of the medical device of clause 12, the outer surface of the medial portion of the hub expands outwardly from the longitudinal axis as the medial portion meets the proximal portion of the hub.

Clause 14: In some examples of the medical device of any of clauses 1-13, a distal portion of the hub lumen is configured to fixedly receive the proximal end of the catheter body.

Clause 15: In some examples of the medical device of any of clauses 1-14, the medical device further includes the catheter body.

Clause 16: In one example, a method includes positioning a proximal end of a catheter body adjacent to a distal end of a hub, wherein the hub defines a hub lumen extending along a longitudinal axis of the hub from a proximal portion of the hub to the distal portion, wherein an outer surface of the distal portion of the hub tapers inwardly toward the longitudinal axis as the distal portion extends distally; sliding a strain relief proximally over the catheter body via a strain relief lumen, wherein the strain relief comprises a distal portion and a proximal portion configured to receive the distal portion of the hub within the strain relief; and securing the strain relief to the hub by sliding the proximal portion of the strain relief over the distal portion of the hub, wherein the strain relief lumen substantially aligns with the hub lumen upon the strain relief being secured to the hub, wherein both an outer surface of the strain relief and an outer surface of a medial portion of the hub define a substantially similar distance to the longitudinal axis along an interface between the outer surface of the strain relief and the outer surface of the hub.

Clause 17: In some examples of the method of clause 16, the hub comprises a recess comprising a recess surface that is a smaller distance from the longitudinal axis immediately proximal to the distal portion of the hub and wherein an inner surface of the strain relief comprises one or more flanges sized and shaped to extend into the recess, wherein securing the strain relief to the hub includes the recess of the hub receiving the one or more flanges of the strain relief.

Clause 18: In some examples of the method of clause 16 or clause 17, the proximal portion of the strain relief receives the distal portion of the hub with an interference fit between the outer surface of the distal portion of the hub and an inner surface of the proximal portion of the strain relief.

Clause 19: In some examples of the method of any of clauses 16-18, the method further includes securing a Luer lock at a proximal end of the hub to another medical component.

Clause 20: In some examples of the method of any of clauses 16-19, a force that is required to proximally move the strain relief over the distal portion of the hub to receive the distal portion of the hub increases as the strain relief moves proximally over the distal portion due to the taper of the outer surface of the distal portion of the hub.

Clause 21: In some examples of the method of any of clauses 16-20, the method further includes: inserting the proximal end of the catheter body into a catheter cavity defined at least in part by the distal portion of the hub in response to positioning the proximal end of the catheter body adjacent the distal end of the hub; and fixedly securing the proximal end of the catheter body to a sidewall of the catheter cavity in response to inserting the proximal end of the catheter body into the catheter cavity.

Clause 22: In some examples of the method of clause 21, the sliding the strain relief proximally over the catheter body via the strain relief lumen is in response to fixedly securing the proximal end of the catheter body to a sidewall of the catheter cavity.

Clause 23: In some examples of the method of clause 21 or clause 22, the method further includes fixedly securing the proximal end of the catheter body to the sidewall of the catheter cavity further comprises inserting an adhesive through an adhesive port that extends radially from an outer surface of the distal portion to the catheter cavity.

Clause 24: In some examples of the method of any of clauses 16-23, the method further includes sliding the strain relief in the distal direction over the proximal end of the catheter body to thereby position the strain relief on the catheter body, before attaching the proximal end of the catheter body to the hub and subsequently sliding the strain relief in the proximal direction to facilitate attachment of the strain relief to the hub.

Clause 25: In some examples a device may include the ornamental design for a hub and strain relief as shown and described herein.

The details of one or more aspects of the disclosure are set forth in the accompanying drawings and the description below. Other features, objects, and advantages of the systems and techniques described in this disclosure will be apparent from the description and drawings, and from the claims.

BRIEF DESCRIPTION OF THE DRAWINGS

FIG. 1A is a conceptual diagram illustrating a top view of an example hub and example strain relief secured to an example catheter body.

FIG. 1B is a conceptual diagram illustrating a side view of the hub, strain relief, and catheter body of FIG. 1A.

FIG. 1C is a conceptual diagram illustrating a cross-sectional view of the catheter of FIG. 1A as viewed from the cut-plane of FIG. 1A.

FIG. 3A is a conceptual diagram illustrating a cross-sectional top view of the hub and strain relief of FIG. 1A removed from each other and viewed from a cut-plane that extends along a longitudinal axis of the catheter.

FIG. 3B is a conceptual diagram illustrating a cross-sectional side view of the hub and strain relief of FIG. 1A removed from each other and viewed from the cut-plane that extends along a longitudinal axis of the catheter.

DETAILED DESCRIPTION

Figure 2A:
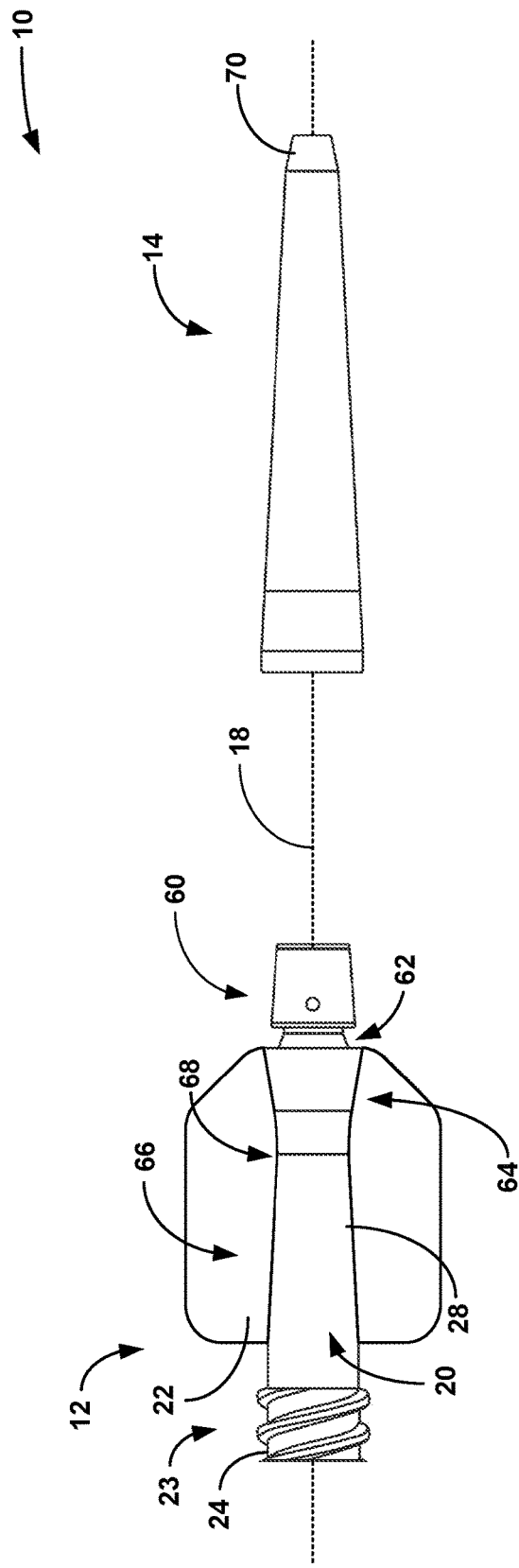
FIG. 2A is a conceptual diagram illustrating a top view of the hub and strain relief of FIG. 1A removed from each other.

In general, the disclosure describes an example medical device or catheter that includes a hub and a strain relief. The hub and strain relief may be configured for use with a medical catheter ("catheter"). Catheters as discussed herein are configured to be navigated through vasculature of a patient to facilitate the delivery of a medical device or a therapeutic substance to a target site within the patient or the aspiration of material from a blood vessel or other part of a patient. A catheter may include a relatively flexible elongated body (e.g., the body of the catheter) that defines one or more longitudinal lumens through which the medical device or therapeutic substance is delivered or through which material is aspirated. The hub and strain relief may be configured to be secured to a proximal end of the catheter. As secured to the catheter, the hub may define a proximal port that provides access to the one or more lumens of the catheter. Further, the strain relief may be configured to surround and support a proximal portion of the catheter and extend distally from the proximal end of the catheter to reduce an amount of strain that is applied to the proximal portion of the catheter during use. The strain relief may help connect the hub to the catheter, help maintain the connection between the hub and the catheter while the hub and/or catheter are experiencing applied forces, or both.

A proximal portion of the strain relief is configured to receive a distal portion of the hub. The strain relief may receive the hub such that a lumen of the hub is substantially aligned (e.g., aligned or nearly aligned) with a lumen of the strain relief. The lumens of the strain relief and hub may align in such a way that the lumen of the catheter will substantially align with (e.g., align with or nearly align with) the lumens of the strain relief and hub when the proximal end of the catheter is secured to the hub and strain relief. These lumens may extend parallel to or be coaxial with a shared longitudinal axis of the hub, strain relief, and catheter.

The strain relief and hub may be dimensioned such that, when the strain relief receives the hub, an outer surface of the hub is a similar radial distance from the longitudinal axis as an outer surface of the strain relief at an interface between the hub and strain relief. Put differently, the strain relief and hub may be dimensioned such that when the strain relief receives the hub, the interface of the strain relief and hub substantially avoids defining ridges or ledges that extend out from a perimeter of hub and/or strain relief and produce a smooth and/or tactile transition between the strain relief and the hub.

As a result of the strain relief and hub radially aligning at an interface between the two to avoid defining ridges or ledges, the strain relief and hub may reduce or eliminate a possibility of a feature of the hub and/or strain relief "catching" or getting "snagged" on an element of an environment of the hub and strain relief and thereby imparting a force upon the hub, strain relief, and/or catheter secured to the hub and strain relief. Such a force could be sudden, or it could arise gradually, in which case the strain relief and/or hub could begin dragging another object on the table, causing resistance as the catheter is advanced into or retracted from the patient. The physician might incorrectly attribute the resistance experienced to the catheter or an associated device being stuck in the body, which could delay the procedure. By reducing or eliminating a chance of the hub and/or strain relief getting caught on an object of the environment and therein imparting a sudden force on the hub and strain relief and catheter, the hub and strain relief may be configured to reduce or eliminate a chance of such sudden force disrupting or otherwise causing a complication in the process of, e.g., a clinician manipulating a distal portion of the catheter within a patient.

As discussed above, the strain relief may be configured to be secured to the hub at least in part as a result of the distal portion of the hub being received by the strain relief. The strain relief may be configured to receive the hub such that a force used to push the distal portion of the hub into the proximal portion of the strain relief increases as the distal portion is inserted into the proximal portion of the strain relief. The strain relief may be configured to receive the hub with an interference fit, where the amount of overlap between the hub and strain relief (and therein the friction of the interference fit and the necessary force to overcome the interference fit) increases as the distal portion of the hub is inserted into the proximal portion of the strain relief. For example, the distal portion of the hub may taper radially inward as the distal portion extends distally, while a cavity of the strain relief that is configured to receive the distal portion of the hub also tapers radially inwardly at a relatively more extreme slope than the distal portion. In this way, as the distal portion of the hub is inserted into the cavity of the strain relief, an amount of contact between the hub and strain relief increases, such that an amount of force required to further insert the distal portion of the hub into the cavity of the strain relief increases.

In some examples, the force to distally push the distal portion of the hub into the cavity may initially be substantially zero as the distal portion of the hub is first inserted into a mouth of the cavity (e.g., as a result of the walls of the cavity, including the mouth of the cavity, initially not contacting the distal portion of the hub as the distal portion is inserted). The force required to insert the distal portion may then increase from this initial substantially zero force to a nominal force (e.g., an amount that a clinician or medical device assembler may easily provide by lightly sliding the distal portion of the hub distally into the cavity) when surfaces of the cavity begin contact the distal portion of the hub. In such examples, the force required to insert the distal portion may increase to an amount that is more than the nominal force as the distal portion is inserted a final relatively short length (e.g., approximately a millimeter) into the cavity of the distal portion immediately prior to full insertion. For example, the distal portion of the hub and the cavity may be dimensioned such that the force required to distally insert the distal portion relative to the hub may be substantially a nominal force until 75% of the distal portion of the hub has been inserted, at which point the force may be relatively greater but still within the bounds of what a clinician or medical device assembler can manually apply. By configuring the hub and strain relief such that a force required to secure the two to each other is a nominal force until the hub and strain relief are nearly fully secured to each other, the hub and strain relief may reduce the difficulty of engaging the distal portion of the hub within the cavity of the strain relief. By reducing the difficulty of engaging the distal portion within the cavity, the hub and strain relief may reduce or eliminate the likelihood of a proximal portion of the catheter being damaged or otherwise strained during the assembly process, that is, during connection of the hub and the strain relief.

FIG. 1A and FIG. 1B are conceptual diagrams illustrating a top and side view, respectively, of an example medical device or catheter 10 that includes hub 12 and strain relief 14. Catheter 10 may additionally include catheter body 16. Hub 12 and strain relief 14 may be removably secured to each other, while one or both of hub 12 and/or strain relief 14 may be fixedly secured to catheter body 16.

Hub 12 may be formed from a relatively stiff material. For example, hub 12 may be made of a polyamide, a polypropylene, a polycarbonate, or the like. As depicted, at least a portion of hub 12 may be substantially symmetrical along longitudinal axis 18 of catheter 10. For example, hub 12 may include a body 20, and body 20 may be radially symmetrical around longitudinal axis 18 of catheter 10.

Hub 12 may also include two wings 22 that extend radially outward from body 20. As depicted in FIGS. 1A and 1B, wings 22 may extend radially outward (e.g., where a radial distance is a straight-line distance from one point to a cross-sectional center point of a longitudinal object and does not necessarily have a connotation of a specific cross-sectional shape) from body 20 of hub 12 along a relatively flat plane, though in other examples (not depicted) wings 22 may define a curve as wings 22 radially extend out away from body 20. Wings 22 may extend out from body 20 on opposite substantially sides of body 20, such that wings 22 are arranged 180° around longitudinal axis 18 relative to each other, though wings 22 may be radially arranged in other manners in other examples. Wings 22 may be configured to provide a surface for a clinician to grip catheter 10 or provide leverage to catheter 10 when manipulating catheter 10. As such, wings 22 may extend a radial distance away from body 20 of hub 12 that is sufficient to enable a finger of a clinician to engage one or both of wings 22. For example, each wing 22 may extend approximately 1 centimeters out from longitudinal axis 18. The specific size, shape, and radial arrangement of wings 22 as depicted and discussed herein is purely for purposes of illustration, as any wings 22 that are consistent with the disclosure herein may be used with hub 12, or hub 12 may omit wings 22.

Hub 12 may terminate at proximal end 23 in a fitting that may be used to couple hub 12 to another medical device. For example, hub 12 may include Luer fitting 24 as depicted in FIGS. 1A and 1B at proximal end 23. Luer fitting 24 may be substantially aligned with longitudinal axis 18 of catheter 10. Using Luer fitting 24, hub 12 may be secured to other medical devices that are configured to introduce a medical device or therapeutic substance into catheter 10 or to remove aspirated material from catheter 10 as described herein.

As discussed above, a distal portion (depicted and further discussed below with reference to FIGS. 2A and 2B) of hub 12 is configured to be received by strain relief 14 (e.g., received by a cavity of strain relief as depicted and further discussed below with reference to FIGS. 3A and 3B). Strain relief 14 may be made of a relatively flexible and soft material to enable strain relief 14 to prevent or reduce strains that may otherwise be applied to catheter body 16 as discussed herein. For example, strain relief 14 may be made of a thermoplastic elastomer. Alternatively, strain relief 14 may be made of polyethylene (PE), low-density polyethylene (LDPE), or the like.

Strain relief 14 may be configured to be releasably secured to hub 12. For example, strain relief 14 may be configured to be secured to hub 12 and removed from hub 12 a plurality of times without substantial damage to either hub 12 or strain relief 14. Strain relief 14 may be configured to be secured to hub 12 such that strain relief 14 and hub 12 may remain secured to each other through normal use of catheter 10 (e.g., use of catheter 10 that is not directed toward separating strain relief 14 and hub 12). Put differently, strain relief 14 may be configured to receive and therein be secured to hub 12 such that strain relief 14 and hub 12 may be removed from each other in response to a purposeful force applied to hub 12 and/or strain relief 14 that is intended to remove hub 12 from strain relief 14 or vice versa but remain secured in the absence of such a purposeful force.

As depicted, strain relief 14 may be configured to receive hub 12 such that outer surface 26 of strain relief 14 and outer surface 28 of hub 12 are at a substantially similar radial distance from longitudinal axis 18 of catheter 10 at interface 30 between outer surfaces 26, 28. Put differently, as depicted in FIGS. 1A and 1B, as secured together, hub 12 and strain relief 14 are configured to define a relatively smooth profile without substantial ridges, bumps, or ledges.

Strain relief 14 may taper radially inward as strain relief 14 extends distally. Strain relief 14 may taper radially inwardly such that, at distal end 32 of strain relief 14, a radial distance between outer surface 26 of strain relief 14 and longitudinal axis 18 may be only nominally greater than a radial distance between outer surface 34 of catheter body 16 and longitudinal axis 18. For example, a radial distance between outer surface 26 of strain relief 14 and longitudinal axis 18 at distal end 32 may be between 0.0075 and 0.02 millimeters greater than a radial distance between outer surface 34 of catheter body 16 and longitudinal axis 18. Put differently, strain relief 14 may be configured to become narrower as strain relief 14 extends distally until the outer surface of strain relief 14 defines a radius that is close to an outer radius of catheter body 16 (e.g., as a radius of strain relief 14 physically must be greater in order to enclose catheter body 16).

Both dimensioning strain relief 14 to narrow to an outer dimension that is substantially similar to an outer dimension of catheter body 16 as well as dimensioning strain relief 14 to define an outer perimeter that is substantially similar to an outer perimeter of hub 12 at an interface between hub 12 and strain relief 14 may reduce or eliminate a possibility of a feature of hub 12 and/or strain relief 14 "catching" or getting "snagged" on an object in an environment of catheter 10 (during movement of catheter 10/strain relief 14 in such environment during a procedure) and therein imparting a sudden force upon catheter 10. By reducing or eliminating a chance of hub 12 and/or strain relief 14 getting caught on an object of the environment and therein imparting a sudden force on catheter 10, hub 12 and strain relief 14 may reduce or substantially eliminate a chance of such sudden force disrupting or otherwise causing a complication in the process of, e.g., a clinician manipulating a distal portion of catheter body 16 within a patient, such as by causing unintentional separation of catheter body 16 and hub 12.

As depicted, catheter body 16 may be an elongated medical catheter. Catheter body 16 may be relatively flexible. Catheter body 16 may be made of a biocompatible polymer, such as, for example, polytetrafluoroethylene (PTFE), low density polyethylene (LDPE), fluoropolymer, perfluoroalkyoxy alkane (PFA), fluorinated ethylene propylene (FEP), a polyether, a polyamide, a polyether block amide, or the like. In some examples, catheter body 16 may be configured to be inserted or implanted into a patient. For example, catheter body 16 may be configured to navigate vasculature of a patient. Once navigated to a target site, catheter body 16 may be used to deliver a medical agent such as a drug or a medical device or a guide wire or the like. For example, a medical agent may be fed through Luer fitting 24 of hub 12 to access catheter body 16.

As depicted in the conceptual diagram of FIG. 1C that illustrates a cross sectional view as taken along cross-sectional plane 36 of FIG. 1A, catheter body 16 may define a lumen 38. Lumen 38 may be configured to provide a longitudinal passageway through catheter body 16 through which a medical device, therapeutic substance, or aspirated material may pass. For example, using the examples above, lumen 38 may be configured to transport a therapeutic or diagnostic substance, such as a drug or contrast agent, and/or lumen 38 may be configured to transport a medical device such as an insertable or implantable medical device, a guidewire, or the like. Though catheter body 16 is depicted with one lumen 38 in FIG. 1C for purposes of clarity, it is to be understood that catheter body 16 may include more than one lumen, and each lumen may be the same size or a different size.

Turning back to FIGS. 1A and 1B, catheter body 16 may define lumen 38 from a proximal end 40 of catheter body 16 to distal end 24 of catheter body 16. Hub 12 and strain relief 14 may also define respective lumens (e.g., as depicted and discussed in more detail below in relation to FIG. 3A). When hub 12 and strain relief 14 are removably secured to each other as depicted in FIGS. 1A and 1B, the lumens of hub 12 and strain relief 14 may substantially align, such that a longitudinal axis of a lumen of hub 12 may be substantially colinear with a longitudinal axis of strain relief 14. Similarly, when proximal end 40 of catheter body 16 is secured to hub 12 and/or strain relief 14, lumen 38 of catheter body 16 may be substantially aligned with the lumens of hub 12. As such, catheter 10 may define longitudinal axis 18 along which each of lumen 38 of catheter body 16 and the lumens of hub 12 and strain relief 14 are centered (e.g., coaxial).

As discussed above, proximal end 40 of catheter body 16 may be fixedly secured to one or both of hub 12 and/or strain relief 16. As discussed herein, proximal end 40 of catheter body 16 may include a proximal tip of catheter body 16 as well as some relatively small length (e.g., one centimeter or less) immediately distal to proximal end 40. In some examples, proximal end 40 of catheter body 16 may only be secured to one of hub 12 or strain relief 14, such that the other of hub 12 or strain relief 14 may be removably secured relative to catheter body 16.

For example, proximal end 40 of catheter body 16 may be friction fit, glued or otherwise bonded (e.g., chemically or heat bonded), or securely fastened to an internal surface that defines the lumen of hub 12. Proximal end 40 of catheter body 16 may be secured to a surface defining the lumen of hub 12 near a distal portion of hub 12. Once proximal end 40 of catheter body 16 is secured to the inner surface of a lumen of hub 12, strain relief 14 may be advanced proximally over distal end 24 of catheter body 16 until strain relief is removably secured to hub 12 and therein catheter body 16 as described herein. In some examples, a surface of lumen of strain relief 14 may include a lubricious coating or may be made of a lubricious material to enable such longitudinal movement over catheter body 16. Once strain relief 14 is removably secured to hub 12 and therein catheter body 16, strain relief 14 may surround proximal portion 42 of catheter body 16. By surrounding proximal portion 42 of catheter body 16, strain relief 14 may reduce or eliminate a chance of catheter body 16 assuming a dramatic angle upon distally extending from hub 12 or otherwise receiving a substantial force at the junction between hub 12 and catheter body 16.

In other examples, proximal end 40 of catheter body 16 may be fixedly secured to strain relief 14. For example, proximal end 40 of catheter body 16 may be fixedly secured to an inner lumen of strain relief 14 at some location distal to hub 12. Proximal end 40 of catheter body 16 may be secured to inner lumen of strain relief 14 using any of the techniques described above (e.g., friction fit, bonding, mechanical connection, or the like). Proximal end 40 of catheter body 16 may be secured at a location where proximal portion 42 of catheter body 16 is surrounded and supported by strain relief 14 as discussed herein.

In other examples, proximal end 40 of catheter body 16 may be fixedly secured to both hub 12 and strain relief 14. For example, proximal end 40 of catheter body 16 may be fixedly secured to a proximal end of an inner lumen of strain relief 14 and a distal end of an inner lumen of hub 12. Proximal end 40 of catheter body 16 may be secured to the inner lumens of hub 12 and strain relief 14 using any of the techniques described above. As secured to the inner lumens of hub 12 and strain relief 14, proximal portion 42 of catheter body 16 may be surrounded and therein supported by strain relief 14 as discussed herein.

Figure 2B:
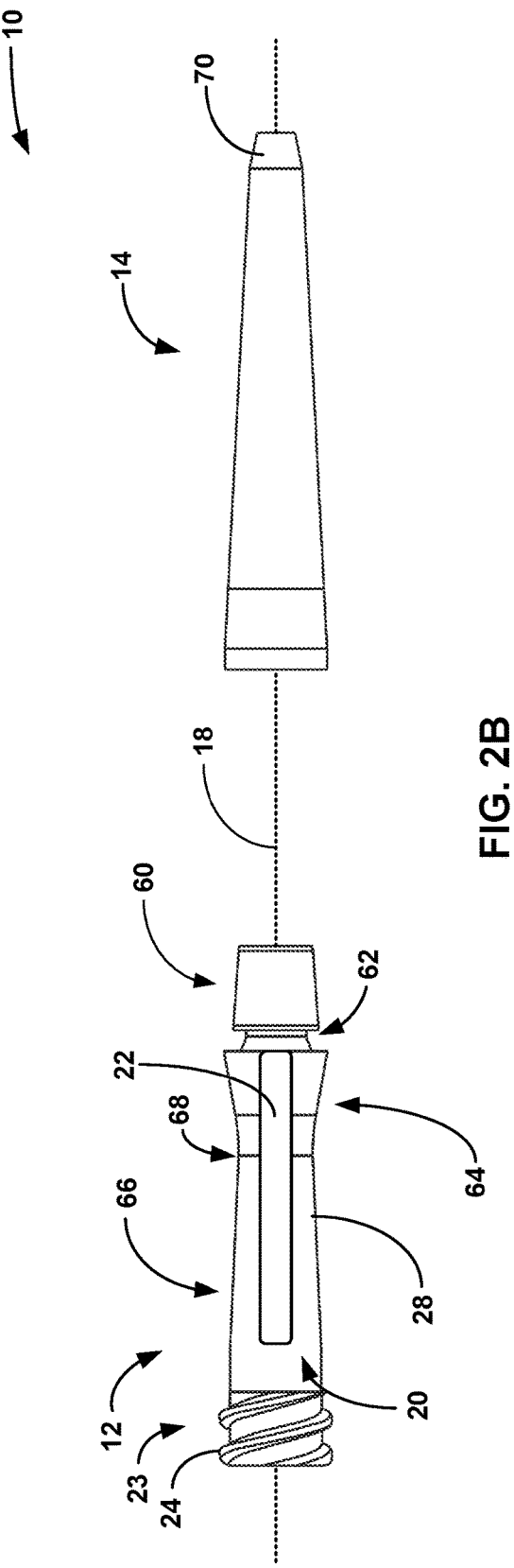
FIG. 2B is a conceptual diagram illustrating a side view of the hub and strain relief of FIG. 1A removed from each other.

FIGS. 2A and 2B are conceptual diagrams illustrating top and side views, respectively, of hub 12 and strain relief 14 separated from each other. As discussed above, a cavity of strain relief 14 may be configured to receive distal portion 60 of hub 12. As depicted, distal portion 60 may include the distal-most feature of hub 12. Distal portion 60 may taper radially inward towards longitudinal axis 18 as distal portion 60 extends distally. Distal portion 60 may be dimensioned to fit within a cavity of strain relief 14 (the cavity of strain relief 14 and interrelation with distal portion 60 are depicted and discussed in greater detail with reference to FIGS. 3A, 3B, and 4). Accordingly, where the cavity is substantially symmetrical around longitudinal axis 18, as depicted in FIGS. 3A and 3B, distal portion 60 may be symmetrical as viewed/rotated around longitudinal axis 18. Dimensioning distal portion 60 (and therein the cavity of strain relief 14) to be symmetrical about longitudinal axis 18 may reduce or substantially eliminate a possibility of incorrectly radially orienting hub 12 and strain relief 14 when inserting distal portion 60 into strain relief 14, therein improving an ease of assembling hub 12 and strain relief 14. In other examples, distal portion 60 may define a nonsymmetrical shape (not depicted), such as a cube, an ellipse, or another keyed shape that facilitates proper orientation of strain relief 14 relative to hub 12.

The outer surface of hub 12 may define recess 62 that extends radially into outer surface 28 of hub 12. Recess 62 may be located proximal to distal portion 60 of hub 12. For example, recess 62 may be immediately proximal to distal portion 60 as depicted in FIGS. 1A and 1B. Recess 62 may extend inward toward longitudinal axis 18 of hub 12 along a perimeter of hub 12. Recess 62 may be configured to receive one or more flanges of strain relief 14 that are configured to extend radially in from an inner surface of strain relief 14 along a proximal portion of strain relief 14 (one or more flanges depicted and discussed in greater detail with reference to FIGS. 3A, 3B, and 5). In this way, the transition between recess 62 and distal portion 60 may define a surface that engages with the one or more flanges of strain relief 14 to maintain the connection of hub 12 and strain relief 14. When strain relief 14 is connected to hub 12, the proximal end of strain relief 14 surrounds recess 62.

Hub 12 may include medial portion 64. Medial portion 64 is a portion of body 20 of hub 12 that is in a middle longitudinal region of hub 12. Medial portion 64 may be immediately proximal to recess 62, such that medial portion 64 abuts with strain relief 14 when distal portion 60 is received by strain relief 14. Where medial portion 64 abuts with strain relief 14 when distal portion 60 is received by strain relief 14, medial portion 64 may define the section of outer surface 28 that is at a same radial distance from longitudinal axis 18 as the adjacent portion of outer surface 26 of strain relief 14.

At least a portion of medial portion 64 may taper inwardly toward longitudinal axis 18 as medial portion 64 extends proximally. For example, medial portion 64 may taper inwardly until intersection 68 with proximal portion 66 of hub 12. Proximal portion 66 may be a longitudinal portion of body 20 of hub 12 that is in a proximal area of hub 12. Proximal portion 66 may define a substantially similar radial distance from longitudinal axis 18 of hub 12 as medial portion 64 at intersection 68. From intersection 68, proximal portion 66 may taper radially outward as proximal portion 66 extends proximally. Proximal portion 66 may taper radially outward until near or at the location where proximal portion 66 intersects with Luer fitting 24.

In some cases, the tapers of medial portion 64 and proximal portion 66 may define a depression or narrower section of body 20 that is dimensioned to comfortably receive a finger of a clinician. Put differently, medial portion 64 and proximal portion 66 may be ergonomically shaped for a clinician to comfortably hold hub 12 and therein handle hub 12 and catheter 10 by placing two fingers (e.g., a thumb and pointer finger) at intersection 68 on opposite sides of hub 12 (e.g., such that these two fingers press against flat surface of wings 22 when contacting intersection 68). Dimensioning hub 12 to define an ergonomic shape for fingers of a clinician may improve an ability of the clinician to grip and manipulate catheter 10, therein improving an effectiveness of catheter 10.

As discussed herein, strain relief 14 may taper radially inward toward longitudinal axis 18 as strain relief 14 extends distally. In some examples, strain relief 14 may taper radially inwardly at a constant slope (or otherwise) until distal tip 70 of strain relief 14. For example, strain relief 14 may taper from an outer radius of between approximately 0.2 centimeters and about 0.5 centimeters (such as approximately 0.35 centimeters) at a proximal edge of strain relief 14 to an outer radius of between approximately 0.1 centimeters and about 0.25 centimeters (such as approximately 0.18 centimeters) at the proximal edge of distal tip 70 over a longitudinal length of between approximately 2 centimeters and about 5 centimeters (such as approximately 3.5 centimeters) (e.g., at an average rate of radially tapering inward 0.050 centimeters for every longitudinal centimeter). In some examples, at distal tip 70, strain relief 14 may taper at a relatively greater slope toward longitudinal axis 18. For example, strain relief 14 may taper inward from an outer radius of between approximately 0.18 centimeters and about 0.22 centimeters (such as approximately 0.20 centimeters) at a proximal edge of distal tip 70 to an outer radius of between approximately 0.12 centimeters and about 0.16 centimeters (such as approximately 0.14 centimeters), or between approximately 0.05 centimeters and 0.20 centimeters, at a distal edge of distal tip 70 over a longitudinal length of between approximately 0.23 centimeters and about 0.27 centimeters (such as approximately 0.25 centimeters). In this way, strain relief 14 may taper radially inward at a rate of approximately 0.21 centimeters inward for every longitudinal centimeter.

Increasingly a rate of inward tapering at distal tip 70 may increase a robustness of strain relief 14 (and therein an ability of strain relief 14 to relieve and/or reduce forces applied to catheter body 16) along the length of strain relief 14 while also narrowing an outer profile of strain relief 14 such that the radius of distal tip 70 is only nominally more than the outer radius of catheter body 16. As discussed above, dimensioning strain relief 14 such that distal tip 70 narrows to an outer radius that is only nominally more than an outer radius of catheter body 16 may reduce or eliminate a possibility of a radially outward extending lip between catheter body 16 and distal tip 70 catching or getting snagged on an object of an environment of catheter 10 and therein imparting a sudden force upon catheter 10. By reducing or eliminating a chance of a lip between distal tip 70 and catheter body 16 getting caught on an object of the environment and therein imparting a sudden force on catheter 10, strain relief 14 may be configured to reduce or eliminate a chance of such sudden force disrupting or otherwise causing a complication in the process of, e.g., a clinician manipulating a distal portion of catheter body 16 within a patient.

FIGS. 3A and 3B are conceptual and schematic diagrams illustrating cross-sectional top and side views, respectively, of the hub and strain relief of FIG. 1A as removed from each other. The cross-sections depicted in FIGS. 3A and 3B are taken along longitudinal axis 18. As depicted, hub 12 defines hub lumen 90. Hub lumen 90 may be substantially symmetric around longitudinal axis 18 in some examples, though in other examples hub lumen 90 may define one or more spaces that are not symmetric around longitudinal axis 18 (not depicted). Hub lumen 90 extends longitudinally throughout a length of hub 12. Hub lumen 90 may be configured to receive medical devices, therapeutic substances, or aspirated material as described herein. In some examples, hub lumen 90 may taper inwardly as hub lumen 90 extends distally from mouth 92 to create a funnel shape, especially where hub lumen 90 and/or hub 12 generally is configured with a Luer fitting. Dimensioning hub lumen 90 to taper inwardly as hub lumen 90 extends distally to create a funnel shape may reduce a difficulty of inserting medical devices or therapeutic substances into hub lumen 90 from mouth 92 of hub lumen 90. In some examples, hub lumen 90 may be coated with a lubricious material to further reduce such a difficulty.

In some examples, hub lumen 90 may include catheter cavity 94 at distal end of hub lumen 90. Catheter cavity 94 may be a space that is configured to receive a proximal end 40 of catheter body 16 (see FIGS. 1A and 1B). For example, catheter cavity 94 may have an outer radius that is substantially similar to an outer radius of catheter body 16. Hub lumen 90 may taper from mouth 92 to an internal radius that is smaller than the radius of catheter cavity 94, at which longitudinal location hub lumen 90 may abruptly increase in radius. Put differently, catheter cavity 94 may define proximal wall 96 that extends radially in from sidewall 100 toward longitudinal axis 18 at a proximal end of catheter cavity 94. As a result of proximal wall 96, a medical device assembler who proximally inserts a proximal end (e.g., proximal end 40 of FIGS. 1A and 1B) of catheter body 16 into hub lumen 90 may be prevented from pushing catheter body 16 past catheter cavity 94 (e.g., such that proximal wall 96 may be configured to be a proximal hard stop for proximal end 40 of catheter body 16 as proximally inserted into hub lumen 90). Once proximal end 40 of catheter body 16 is engaged with proximal wall 96, catheter body 16 may be fixedly secured to the wall of catheter cavity 94 via, e.g., an adhesive injected into hub lumen 90 or due to a relatively tight friction fit between outer surface of catheter body 16 and the wall of catheter cavity 94. For example, an adhesive may be injected through adhesive port 98 to fixedly secure distal end 40 of catheter body 16 to sidewall 100 of catheter cavity 94.

Strain relief 14 defines strain relief lumen 102. Strain relief lumen 102 may be substantially symmetric around longitudinal axis 18. In other examples, strain relief lumen 102 may define more spaces or elements that are not symmetric around longitudinal axis 18 (not depicted). Strain relief lumen 102 extends longitudinally along a length of strain relief 14. Strain relief lumen 102 is configured to receive catheter body 16 such that strain relief 14 surrounds catheter body 16 (e.g., radially or circumferentially surrounds catheter body 16). In some examples, strain relief lumen 102 may define a substantially cylindrical shape along length of strain relief lumen 102 to better contact catheter body 16 along this length (e.g., in examples in which an outer surface of catheter body 16 defines a substantially cylindrical shape as distally extending from hub 12). Dimensioning strain relief lumen 102 to define a shape that is similar to the shape of a proximal portion catheter body 16 (e.g., proximal portion 42 as depicted in FIGS. 1A and 1B) may increase an ability of strain relief 14 to reduce or eliminate unwanted forces upon catheter body 16 and/or maintain catheter body 16 in this preferred shape.

Figure 5:
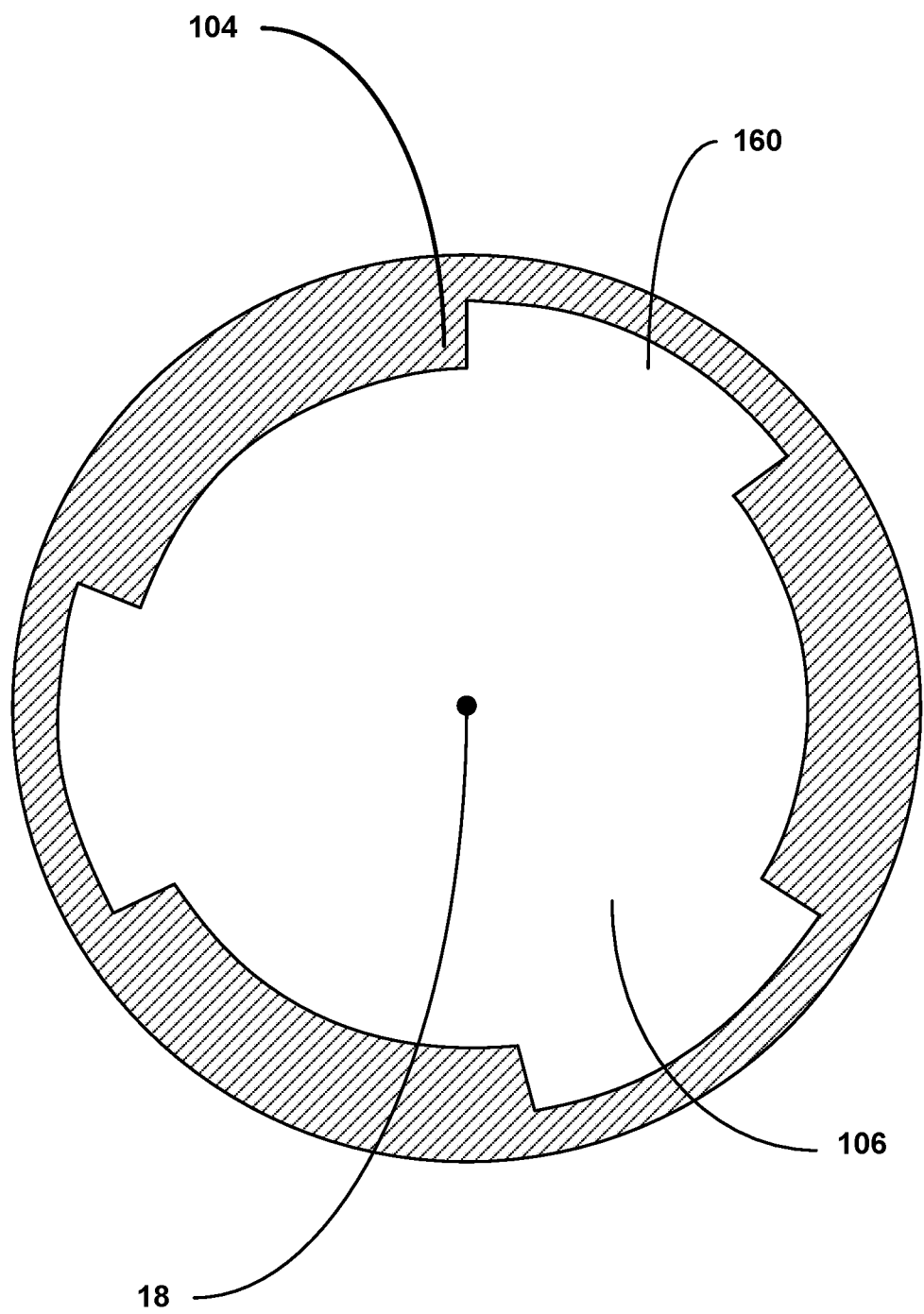
FIG. 5 is a conceptual diagram illustrating a cross-sectional view of the strain relief of FIG. 1A and viewed from the cut-plane of FIG. 3A.

In some examples, strain relief lumen 102 may be partially asymmetrical as a result of flanges 104 extending radially into strain relief lumen 102. Flanges 104 may extend in along a perimeter of strain relief lumen 102. As discussed herein, flanges 104 may include one or more flanges 104 that each extend radially in from a portion of a perimeter of strain relief lumen 102. Each of flanges 104 may be configured to be received by recess 62, such that each of flanges 104 is around a perimeter of strain relief lumen 102 that is configured to align with recess 62 when strain relief 14 receives distal portion 60 of hub 12. Flanges 104 may be radially arranged around a perimeter of strain relief 102. For example, flanges 104 may be evenly spatially arranged around the perimeter, such that flanges 104 include three flanges 104 that are radially spaced out 120° around a perimeter of strain relief 102 (e.g., as depicted in FIG. 5 as viewed from cross-sectional plan 105 of FIG. 3A).

Strain relief 14 may define cavity 106 adjacent proximal end of strain relief lumen 102. As discussed herein, cavity 106 may be configured to receive distal portion 60 of hub 12 as inserted through mouth 108 of cavity 106 such that a force required to insert distal portion 60 into cavity 106 may increase as distal portion 60 moves distally relative to cavity 106. For example, outer diameter 110 of a distal face of distal portion 60 may be smaller than gap 112 between flanges 104, such that distal portion 60 initially may be inserted past flanges 104 without encountering a resisting force from flanges 104 and/or strain relief 14. Similarly, diameter 114 of a proximal edge of distal portion 60 may be substantially similar to diameter 116 of proximal edge of cavity 106, such that upon being fully inserted proximal edge 114 of distal portion 60 may fit within cavity 106 as engaged by flanges 104. However, the inward-tapering sidewall 118 of cavity 106 may taper inward with a greater than a slope defined by outer surface 120 of distal portion 60.

Figure 4:
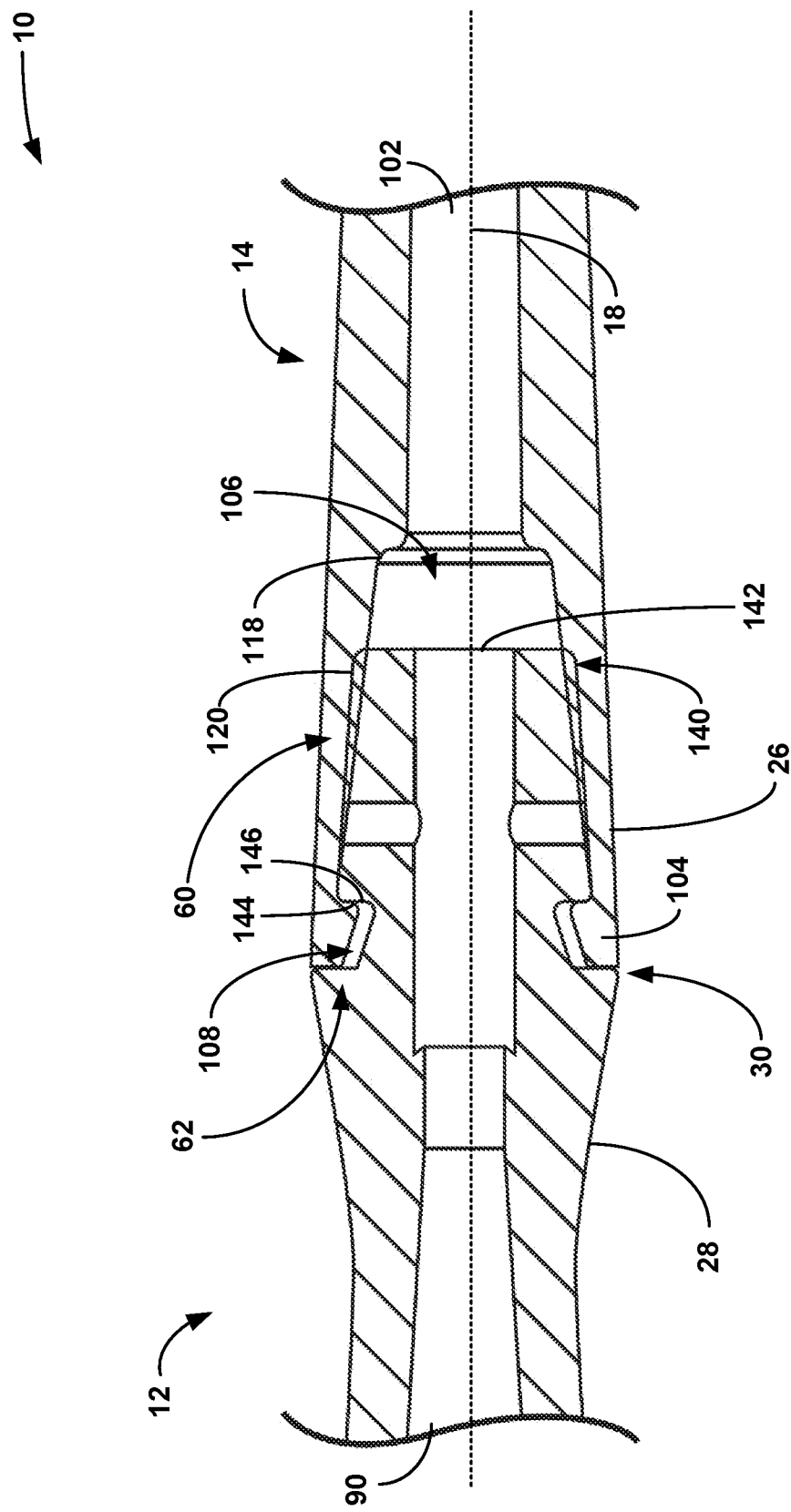
FIG. 4 is a conceptual diagram illustrating a cross-sectional side view of the strain relief receiving the hub of FIG. 1A viewed from the cut-plane that extends along a longitudinal axis of the catheter.

FIG. 4 is a conceptual and schematic diagram illustrating the interference fit of hub 12 and strain relief 14 via a cross-sectional side view along longitudinal axis 18. Specifically, FIG. 4 depicts the interference fit such that outer surface 120 of distal portion 60 is depicted as overlapping sidewall 118 of cavity 106. As depicted, an amount of dimensional overlap 140 between distal portion 60 and sidewall 118 of cavity 106 increases as distal portion 60 extends distally into cavity 106. It is to be understood that as actually constructed, hub 12 and strain relief 14 does not actually define dimensional overlap 140 as depicted, but instead that one or both of hub 12 and/or strain relief 14 deforms when engaged as a result of the interference fit. In some examples, strain relief 14 may deform in response to receiving hub 12 (e.g., as a result of a relatively more flexible material and a relatively thinner wall) while hub 12 substantially does not deform when received by cavity 106.

In some examples, mouth 108 and flanges 104 of strain relief 14 may be configured to facilitate the insertion and subsequent securement of distal portion 60 of hub 12. For example, mouth 108 of cavity 106 and/or flanges 104 may be dimensioned such that distal edge 142 of distal portion 60 may longitudinally extend past mouth 108 without touching any elements of mouth 108 (e.g., such as flanges 104). Because of the relative dimensions of mouth 108, flanges 104, and distal edge 142, the force to distally insert distal portion 60 into cavity 106 may initially be substantially zero. After this initial insertion, the inward taper of sidewall 118 of cavity 106 as well as flanges 104 may increasingly contact and engage distal portion 60 of hub 12 as hub 12 is inserted into cavity 106. For example, the necessary force to distally push distal portion 60 into cavity 106 may increase from zero to a nominal force and then a more-than-nominal force as discussed herein to fully insert distal portion 60 into cavity 106. By dimensioning flanges 104 and distal portion 60 of hub such that a force to insert distal portion 60 into cavity 106 is relatively nominal until distal portion 60 is nearly fully inserted into cavity 106 (causing the one or more flanges 104 to press down upon distal portion 60 during insertion of distal portion 60), hub 12 and strain relief 14 may reduce the difficulty of receiving distal portion 60 within cavity 106.

Upon distal portion 60 being fully inserted into cavity 106, flanges 104 may be configured to secure distal portion 60 within cavity 106. For example, distal face 144 of flanges 104 may extend radially inward to a relatively smaller radius than proximal face 146 of distal portion 60 of hub 12. Distal face 144 of flanges 104 may provide a stabilizing force on proximal face 146 of distal portion 60 to secure hub 12 to strain relief 14. This stabilizing force, along with a stabilizing force provided by the interference fit, may be sufficient to secure hub 12 to strain relief 14 throughout use of catheter 10. By reducing the difficulty of receiving hub 12 within strain relief 14 while configuring strain relief 14 to secure distal portion 60 once received, hub 12 and strain relief 14 may reduce or eliminate the likelihood of proximal portion 42 of catheter body 16 being damaged or otherwise strained as a result of a such difficulty.

As discussed herein and depicted in FIG. 4, hub 12 and strain relief 14 may be configured to radially align at interface 30 of outer surface 28 of hub 12 and outer surface 26 of strain relief 14 as a result of flanges 104 extending inward into recess 62. As a result of flanges 104 being configured to be received by recess 62 such that outer surfaces 26, 28 radially align at interface 30, hub 12 and strain relief 14 may reduce or eliminate a possibility of a feature of either hub 12 and/or strain relief 14 catching or getting snagged on an object of an environment of hub 12 and strain relief 14 and therein imparting a sudden force upon hub 12, strain relief 14, and/or catheter body 16. By reducing or eliminating a chance of hub 12 and/or strain relief 14 getting caught on an object of the environment and therein imparting a sudden force on hub 12, strain relief 14, and/or catheter body 16, hub 12 and strain relief 16 may be configured to reduce or eliminate a chance of such sudden force disrupting or otherwise causing a complication in the process of, e.g., a clinician manipulating a distal portion of catheter body 16 within a patient.

FIG. 5 is a conceptual and schematic diagram illustrating a cross-sectional view of strain relief 14 as viewed from cut-plane 105 of FIG. 3A. FIG. 5 depicts three flanges 104 radially spaced apart around longitudinal axis 18, such that flanges 104 define gaps 106 between radially adjacent flanges 104. In other examples, strain relief 14 may include more or fewer flanges 104. For example, strain relief 14 may include a single flange 104 (not depicted). Where strain relief 14 includes a single flange 104, the single flange 104 may extend around a substantially all of the perimeter.

Figure 6:
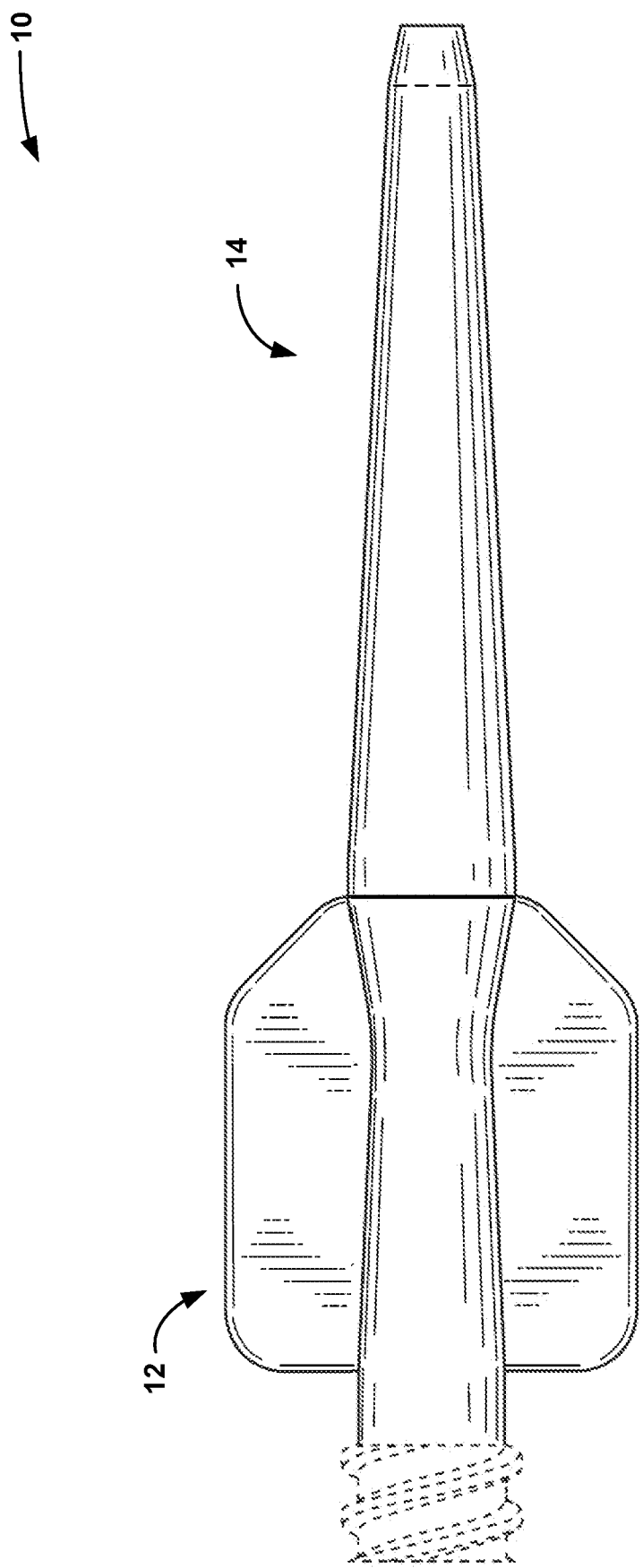
FIG. 6 is a conceptual diagram illustrating a top view of the strain relief receiving the hub of FIG. 1A.
Figure 7:
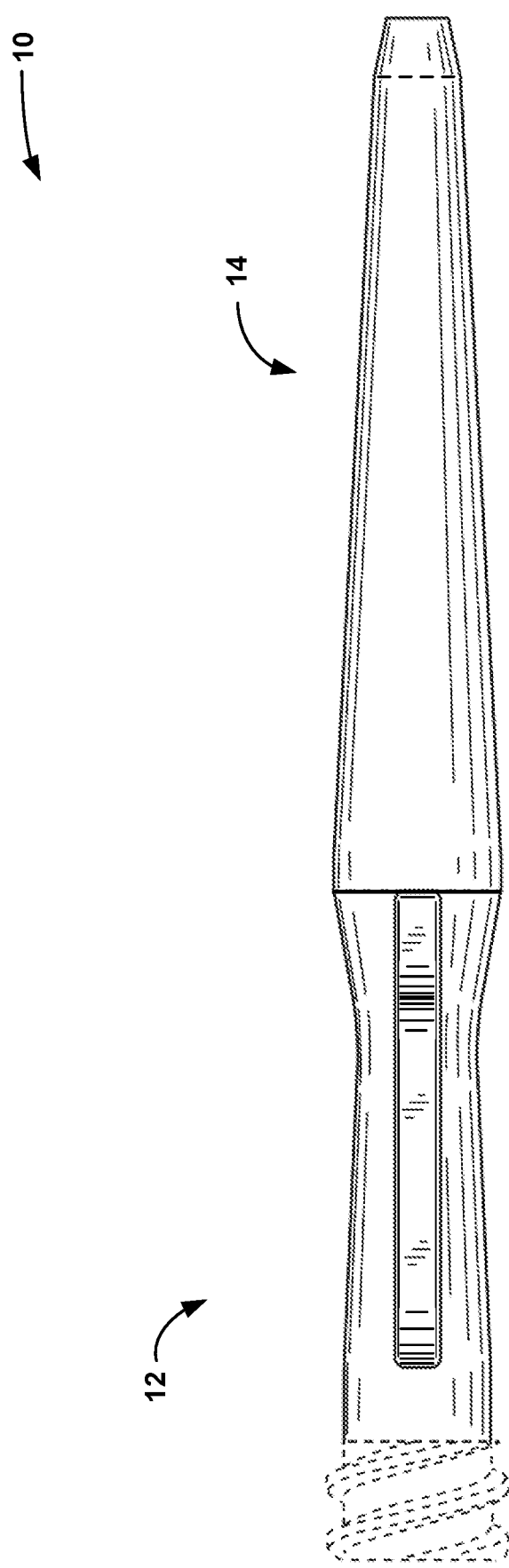
FIG. 7 is a conceptual diagram illustrating a side view of the strain relief receiving the hub of FIG. 1A.
Figure 8:
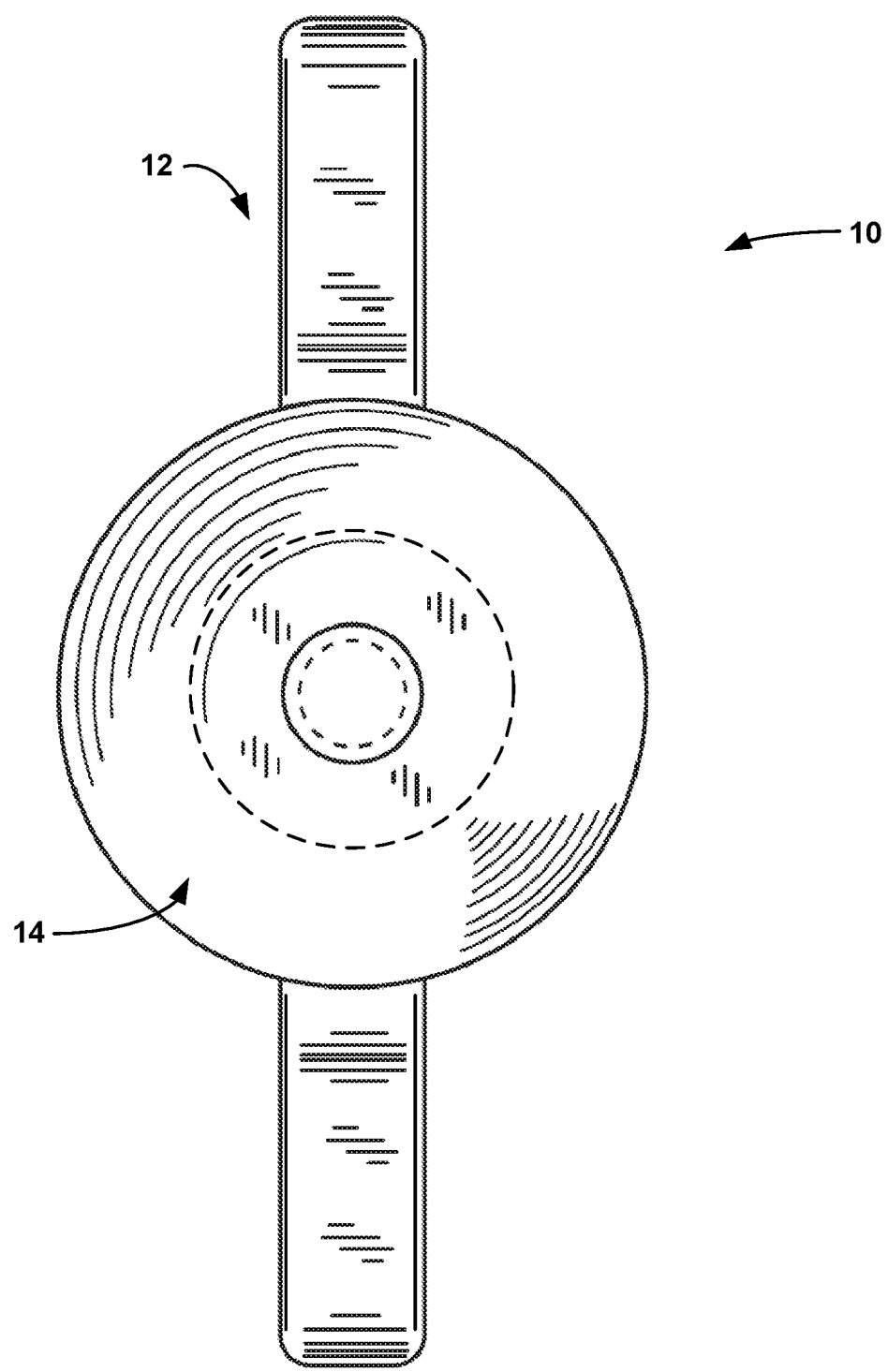
FIG. 8 is a conceptual diagram illustrating a front view from a distal end of the strain relief receiving the hub of FIG. 1A.
Figure 9:
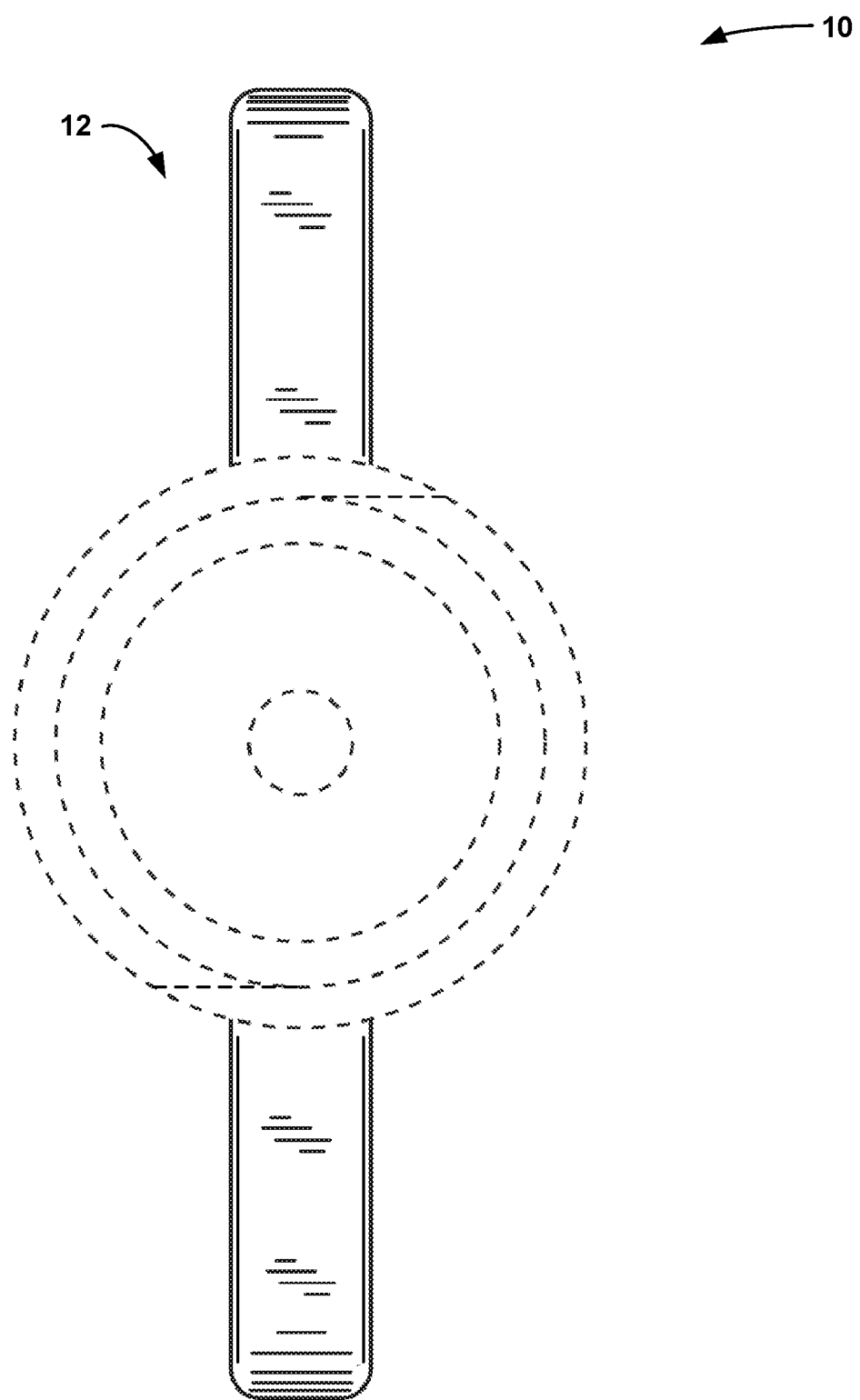
FIG. 9 is a conceptual diagram illustrating a back view from the proximal end of the strain relief as receiving the hub of FIG. 1A.

As discussed herein, hub 12 and strain relief 14 may define shapes that are substantially symmetrical about longitudinal axis 18. Further, edges of hub 12 and strain relief 14 may be rounded or chamfered to make a profile of hub 12 and strain relief 14 relatively more smooth. For example, FIGS. 6-9 are conceptual illustrations of top, side, front, and back views, respectively, of strain relief 14 as having received hub 12 that depict these smooth profiles and interfaces. FIG. 6 is a conceptual diagram illustrating a top view of strain relief 14 receiving hub 12. FIG. 7 is a conceptual diagram illustrating a side view of strain relief 14 receiving hub 12. FIG. 8 is a conceptual diagram illustrating a front view from a distal end of strain relief 14 receiving hub 12. FIG. 9 is a conceptual diagram illustrating a back view from the proximal end of strain relief 14 as receiving hub 12.

Figure 10:
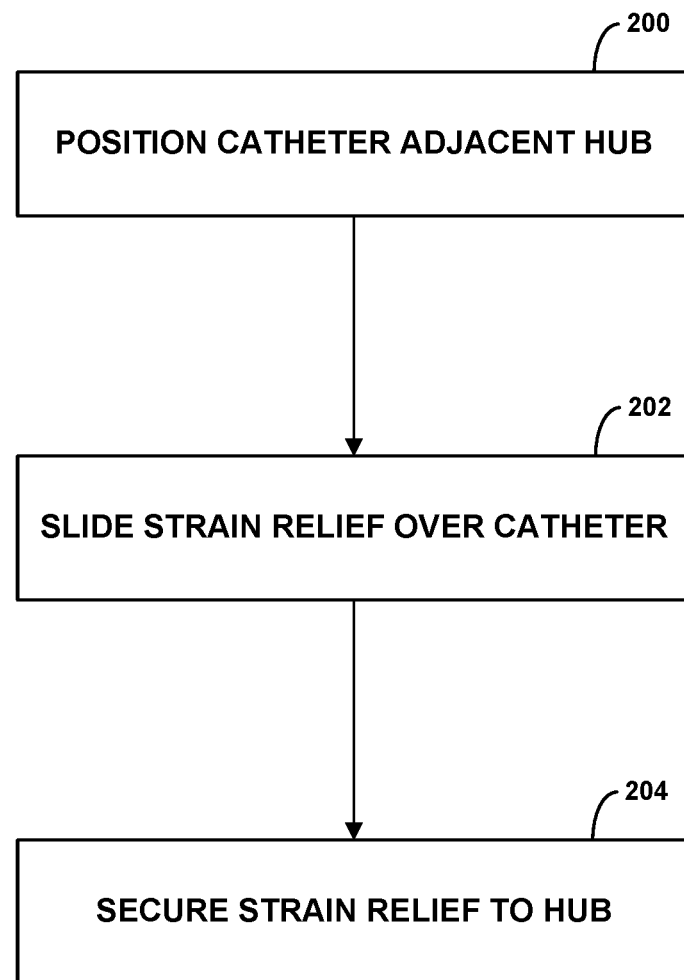
FIG. 10 is a flow diagram of an example method of assembling the catheter, hub, and strain relief of FIG. 1A.

FIG. 10 is a flow diagram of an example method of assembling catheter body 16, hub 12, and strain relief 14. Though the method of FIG. 10 is discussed with reference to catheter body 16, hub 12, and strain relief 14, it is to be understood that the techniques described may apply to any devices consistent with this disclosure. Proximal end 40 of catheter body 16 may be positioned adjacent to hub 12 (200). Proximal end 40 of catheter body 16 may be positioned adjacent distal portion 60 of hub 40. In some examples, proximal end 40 of catheter body 16 may be secured to hub 12. For example, proximal end 40 may be secured to sidewall 100 of catheter cavity 94 of hub 12. Proximal end 40 of catheter body 16 may be secured to hub using an adhesive that fixedly secures catheter body 16 to hub.

Strain relief 14 may be slid over distal end 24 of catheter body 16 (202). Strain relief 14 may be slid proximally along catheter body 16 once catheter body 16 is secured to hub 12. Strain relief 14 may be slid relative to catheter body 16 using a strain relief lumen 102 of strain relief 14.

Strain relief 14 may be secured to hub 12 (204). Cavity 106 of strain relief 14 may receive distal portion 60 of hub 12 to secure strain relief 14 to hub 12. Distal portion 60 may be fully inserted into cavity 106 to secure strain relief 14 to hub 12. In some examples, a user securing strain relief 14 to hub 12 may have to increase a force applied to strain relief 14 and/or hub 12 as strain relief 14 receives hub due to the increasing overlapping dimensions as discussed herein. Once secured, a user may secure another medical component to a fitting such as Luer fitting 24 at a proximal end of hub 12 to enable an agent of the medical component being provided to catheter body 16.

Various examples have been described. These and other examples are within the scope of the following claims.

What is claimed is:

1. A method comprising:
    positioning a proximal end of a catheter body adjacent to a distal end of a hub, wherein the hub defines a hub lumen extending along a longitudinal axis of the hub from a proximal portion of the hub to the distal portion, wherein an outer surface of the distal portion of the hub tapers inwardly toward the longitudinal axis as the distal portion extends distally;
    sliding a strain relief proximally over the catheter body via a strain relief lumen, wherein the strain relief comprises a distal portion and a proximal portion configured to receive the distal portion of the hub within the strain relief; and
    securing the strain relief to the hub by at least sliding the proximal portion of the strain relief over the distal portion of the hub, wherein the strain relief lumen substantially aligns with the hub lumen upon the strain relief being secured to the hub, wherein both an outer surface of the strain relief and an outer surface of a medial portion of the hub define a substantially similar distance to the longitudinal axis along an interface between the outer surface of the strain relief and the outer surface of the medial portion of the hub.

2. The method of claim 1, wherein the hub comprises a recess comprising a recess surface that is a smaller distance from the longitudinal axis immediately proximal to the distal portion of the hub and wherein an inner surface of the strain relief comprises one or more flanges sized and shaped to extend into the recess, wherein securing the strain relief to the hub includes the recess of the hub receiving the one or more flanges of the strain relief.

3. The method of claim 1, wherein the proximal portion of the strain relief receives the distal portion of the hub with an interference fit between the outer surface of the distal portion of the hub and an inner surface of the proximal portion of the strain relief.

4. The method of claim 1, further comprising securing a Luer lock at a proximal end of the hub to another medical component.

5. The method of claim 1, wherein a force that is required to proximally move the strain relief over the distal portion of the hub to receive the distal portion of the hub increases as the strain relief moves proximally over the distal portion due to the taper of the outer surface of the distal portion of the hub.

6. The method of claim 1, further comprising:
    inserting the proximal end of the catheter body into a catheter cavity defined at least in part by the distal portion of the hub in response to positioning the proximal end of the catheter body adjacent the distal end of the hub; and
    fixedly securing the proximal end of the catheter body to a sidewall of the catheter cavity in response to inserting the proximal end of the catheter body into the catheter cavity.

7. The method of claim 6, wherein the sliding the strain relief proximally over the catheter body via the strain relief lumen is in response to fixedly securing the proximal end of the catheter body to a sidewall of the catheter cavity.

8. The method of claim 6, wherein fixedly securing the proximal end of the catheter body to the sidewall of the catheter cavity further comprises inserting an adhesive through an adhesive port that extends radially from an outer surface of the distal portion to the catheter cavity.

9. The method of claim 1, further comprising sliding the strain relief in the distal direction over the proximal end of the catheter body to thereby position the strain relief on the catheter body, before attaching the proximal end of the catheter body to the hub and subsequently sliding the strain relief in the proximal direction to facilitate attachment of the strain relief to the hub.

\* \* \* \* \*